US008642789B2

(12) United States Patent
Tu et al.

(10) Patent No.: US 8,642,789 B2
(45) Date of Patent: Feb. 4, 2014

(54) CO-CRYSTAL COMPOUND, METHOD FOR PREPARING THE SAME AND OXIDANT OF GAS GENERATOR PROPELLANT

(75) Inventors: Lee Tu, Flushing, NY (US); Jeng-Wei Chen, Keelung (TW)

(73) Assignee: National Central University, Jhongli (TW)

(*) Notice: Subject to any disclaimer, the term of this patent is extended or adjusted under 35 U.S.C. 154(b) by 260 days.

(21) Appl. No.: 13/354,993

(22) Filed: Jan. 20, 2012

(65) Prior Publication Data

US 2013/0102797 A1    Apr. 25, 2013

(30) Foreign Application Priority Data

Oct. 25, 2011    (TW) .............................. 100138749 A

(51) Int. Cl.
*C07D 321/00*    (2006.01)
*C07D 493/00*    (2006.01)

(52) U.S. Cl.
USPC ........................................................ 549/351

(58) Field of Classification Search
USPC ........................................................ 549/351
See application file for complete search history.

(56) References Cited

PUBLICATIONS

Durant et al, Jol. Chem. Soc. Dalton Trans. (1992) pp. 3399-3400.*
Atkinson, Manza Battle Joshua. "Fundamentals and applications of co-crystal methodologies: reactivity, structure determination, and mechanochemistry." PhD diss., University of Iowa, 2011.*
Ganin et al CrystEngComm, 2011, 13, 674-683.*

* cited by examiner

*Primary Examiner* — Andrew D Kosar
*Assistant Examiner* — Raymond Covington
(74) *Attorney, Agent, or Firm* — Wang Law Firm, Inc.; Li K. Wang; Stephen Hsu

(57) ABSTRACT

A co-crystal compound containing ammonium nitrate and benzo-18-crown-6-ether. Ammonium nitrate and benzo-18-crown-6-ether are used to form the co-crystal compound with hydrogen bonding in a mole ratio of 1:1. A melting point of the co-crystal compound falls within a range of 124~130° C., and the co-crystal compound can be prepared by an evaporation method or an anti-solvent method. The co-crystal compound comes with a non-hygroscopic property, a low burning rate (7 MPa, 0.58 mm/s) and a high pressure index (n>0.6), which can be used for replacing the oxidizer of a common gas generator propellant.

10 Claims, 9 Drawing Sheets

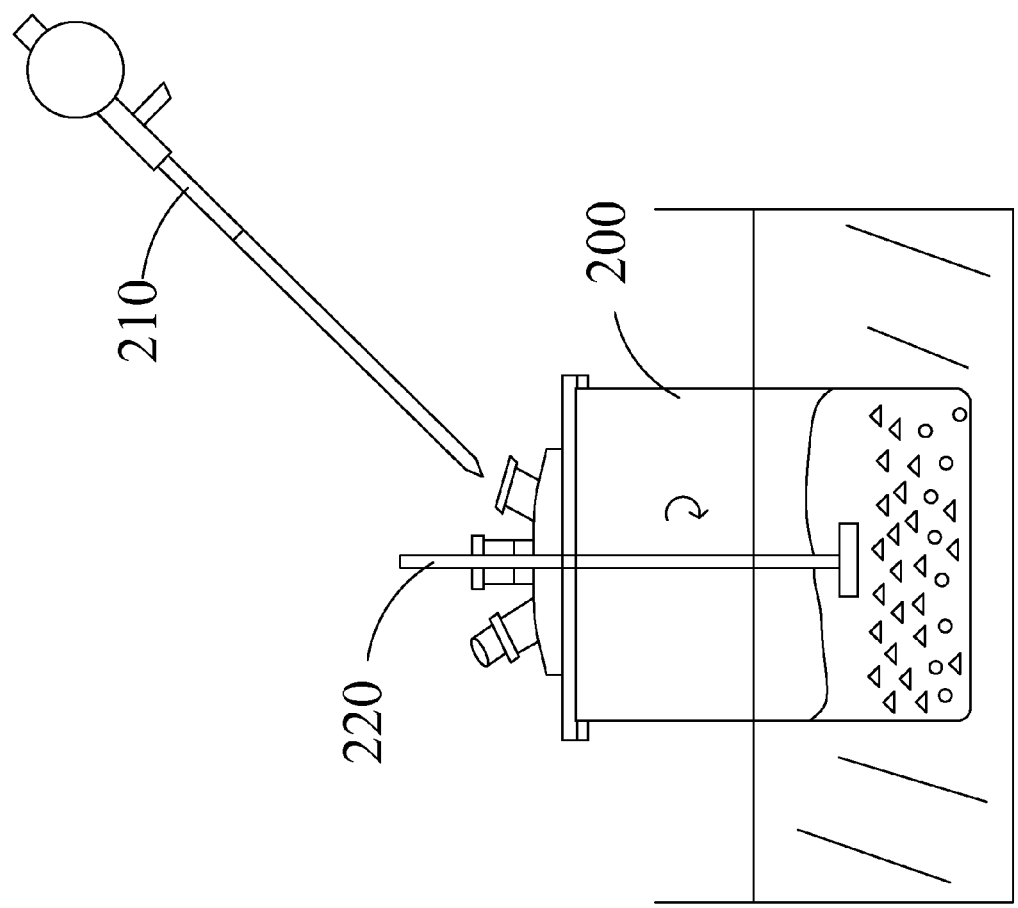

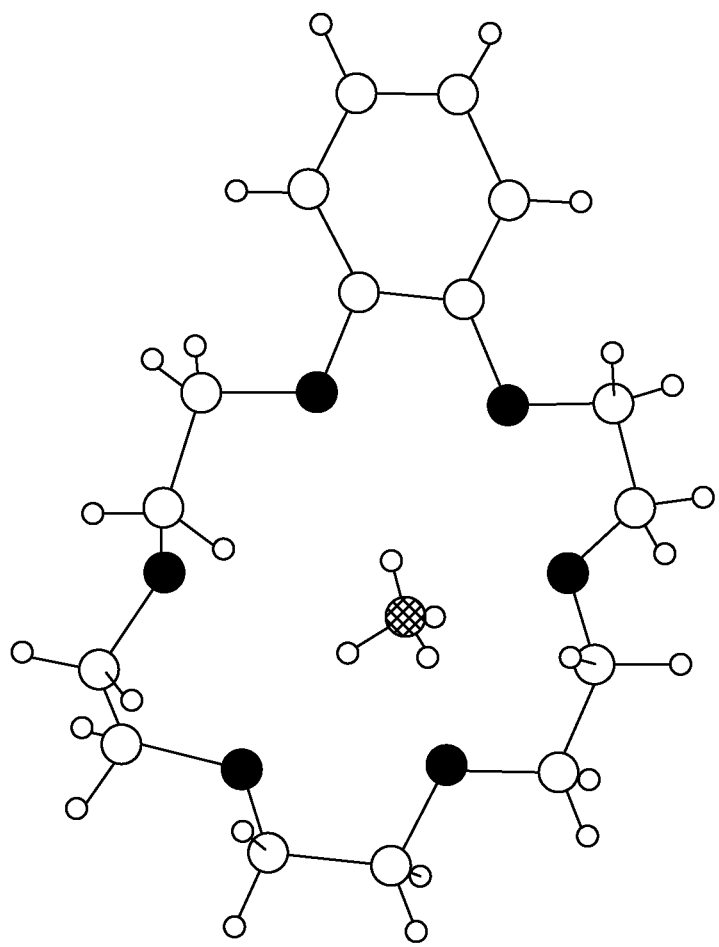
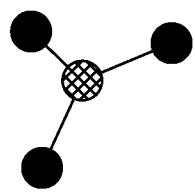
FIG. 3

CO-CRYSTAL COMPOUND, METHOD FOR PREPARING THE SAME AND OXIDANT OF GAS GENERATOR PROPELLANT

CROSS-REFERENCE TO RELATED APPLICATION

This application claims the benefit of priority to Taiwan Patent Application No. 100138749, filed on Oct. 25, 2011, in the Taiwan Intellectual Property Office, the disclosure of which is incorporated herein in its entirety by reference.

BACKGROUND OF THE INVENTION

1. Field of the Invention

The present invention relates to a co-crystal compound, a method for preparing the co-crystal compound, and an oxidizer of a gas generator propellant, in particular to the co-crystal compound formed by an anti-solvent method or an evaporation method, the method for preparing the co-crystal compound, and the oxidizer of the gas generator propellant.

2. Description of the Related Art

After being self-assembled and combined among solutes, a co-crystal compound can produce a saturated solution by different solubilities at different temperatures and reducing the temperature of a high-temperature saturated solution, so that the solutes in the solution are precipitated to form a crystal which is the co-crystal compound.

In general, the co-crystal compound can be used in the traditional pharmaceutical industry mainly because the physical and chemical properties of the co-crystal compound varies with the formation process of the co-crystal compound, and this feature can provide diversified developments to the pharmaceutical industry. For example, the crystalline pattern of the compound is changed to enhance the solubility, bioavailability, and stability. However, using the properties of a co-crystal compound in other industries has not been found yet.

SUMMARY OF THE INVENTION

Therefore, it is a primary objective of the present invention to provide a co-crystal compound, a method for preparing the co-crystal compound, and an oxidizer of a gas generator propellant to improve the utility of the co-crystal compound.

To achieve the aforementioned objective, the present invention provides a co-crystal compound comprising ammonium nitrate and benzo-18-crown-6-ether, wherein ammonium nitrate and benzo-18-crown-6-ether in a specific ratio are used for forming the co-crystal compound with hydrogen bonding, and the specific ratio is a mole ratio approximately equal to 1:1.

Preferably, the co-crystal compound of the present invention is formed by an anti-solvent method or an evaporation method.

If the co-crystal compound of the present invention is formed by the anti-solvent method, a first solvent is used to dissolve ammonium nitrate and benzo-18-crown-6-ether to form a solution, and a second solvent is added into the solution to form the co-crystal compound of the present invention. Wherein, the ratio of the first solvent to the second solvent is approximately equal to 1:3. The first solvent can be methanol or ethanol, and the second solvent can be methyl tertiary butyl ether or ethyl acetate.

Preferably, the co-crystal compound of the present invention has a melting point substantially falling within a range of 124~130° C.

The present invention further provides an oxidizer of a gas generator propellant comprising the aforementioned co-crystal compound.

The present invention further provides a method for preparing the co-crystal compound comprising the steps of: providing ammonium nitrate and benzo-18-crown-6-ether; and using ammonium nitrate and benzo-18-crown-6-ether to form a co-crystal compound by an anti-solvent method; wherein, the anti-solvent method uses a first solvent to dissolve ammonium nitrate and benzo-18-crown-6-ether to form a solution, and adds a second solvent into the solution to form the co-crystal compound.

In summation, the co-crystal compound, the method of preparing the co-crystal, and the oxidizer of the gas generator propellant in accordance with the present invention have the following advantages:

The co-crystal compound of the present invention can be used as an oxidizer of a gas generator propellant.

The technical characteristics and effect of the present invention will become apparent with the detailed description of preferred embodiments accompanied with the illustration of related drawings as follows.

BRIEF DESCRIPTION OF THE DRAWINGS

FIG. 2 is a schematic view of preparing a co-crystal compound of the present invention;

FIG. 3 is a schematic view of the molecular structure of a co-crystal compound of the present invention;

DESCRIPTION OF THE PREFERRED EMBODIMENTS

The technical characteristics of the present invention will become apparent with the detailed description of the preferred embodiments accompanied with the illustration of related drawings as follows. It is noteworthy to point out that same numerals are used for representing respective elements for the description of the preferred embodiments and the illustration of the drawings.

Figure 1A:
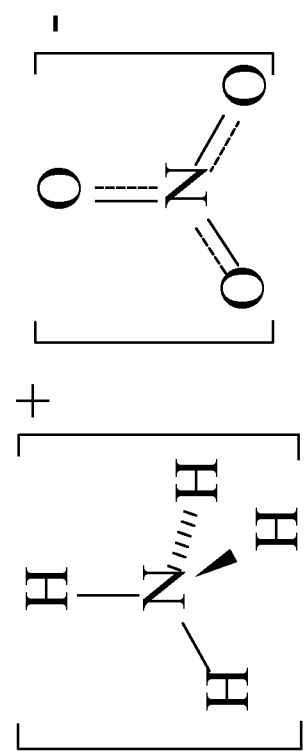
FIG. 1A is a schematic view of the atomic arrangement of ammonium nitrate.
Figure 1B:
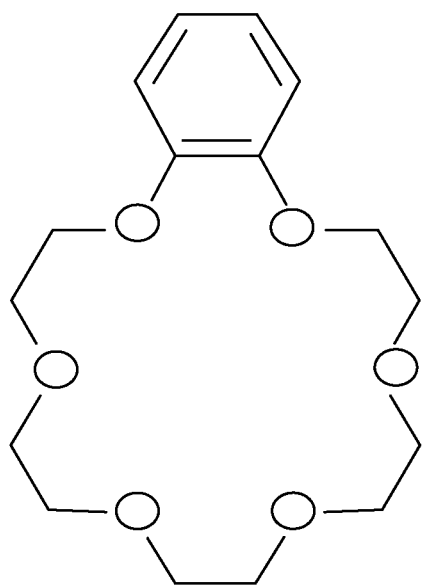
FIG. 1B is a schematic view of the atomic arrangement of benzo-18-crown-6-ether.

With reference to FIG. 1A for a schematic view of the atomic arrangement of ammonium nitrate, FIG. 1B for a schematic view of the atomic arrangement of benzo-18-crown-6-ether, and FIG. 3 for a schematic view of the molecular structure of a co-crystal compound of the present invention, the co-crystal compound contains ammonium nitrate and benzo-18-crown-6-ether, wherein ammonium nitrate and benzo-18-crown-6-ether in specific ratio are used for forming a co-crystal compound having hydrogen bonding.

For example, the co-crystal compound of the present invention can be prepared by an anti-solvent method, and the specific implementation is described below. With reference to FIG. 2 for a schematic view of preparing a co-crystal compound of the present invention, the same mole of ammonium nitrate ($NH_4NO_3$) and benzo-18-crown-6-ether ($C_{16}H_{24}O_6$) are prepared and added into a glass reactor 200. In this preferred embodiment, the quantities of both ammonium nitrate and benzo-18-crown-6-ether are equal to 0.048 mole, and then a 25 ml pipette 210 is used to titrate approximately 31 ml of methanol (MeOH) in the glass reactor 200. A water bath takes place in the glass reactor 200 in a water tank at 25° C., and a blender 220 is provided for blending at 250 rpm for two hours., and finally the 25 ml pipette 210 is used for titrate methyl tertiary butyl ether into the glass reactor 200 slowly. Now, the solution in the glass reactor 200 becomes turbid gradually, and then we can wait for the formation of the co-crystal compound of the present invention.

It is noteworthy to point out that the methanol used in the aforementioned method can be substituted by ethanol or any other equivalent compound, and the methyl tertiary butyl ether can be substituted by ethyl acetate or any other equivalent compound. Further, the methanol of this preferred embodiment serves as a good solvent, and methyl tertiary butyl ether serves as a bad solvent. In other words, a good solvent is used for dissolving ammonium nitrate and benzo-18-crown-6-ether evenly, and then a bad solvent is added into ammonium nitrate and benzo-18-crown-6-ether to form the co-crystal compound with a mole ratio of 1:1, wherein hydrogen bonds are formed between ammonium nitrate and benzo-18-crown-6-ether.

In addition, the ratio of the good solvent to the bad solvent falls within a range of 1:1 to 1:10, preferably 1:1 to 1:5, and more preferably 1:2 to 1:4. In this preferred embodiment, the ratio of the good solvent to the bad solvent is approximately equal to 1:3.

Figure 5:
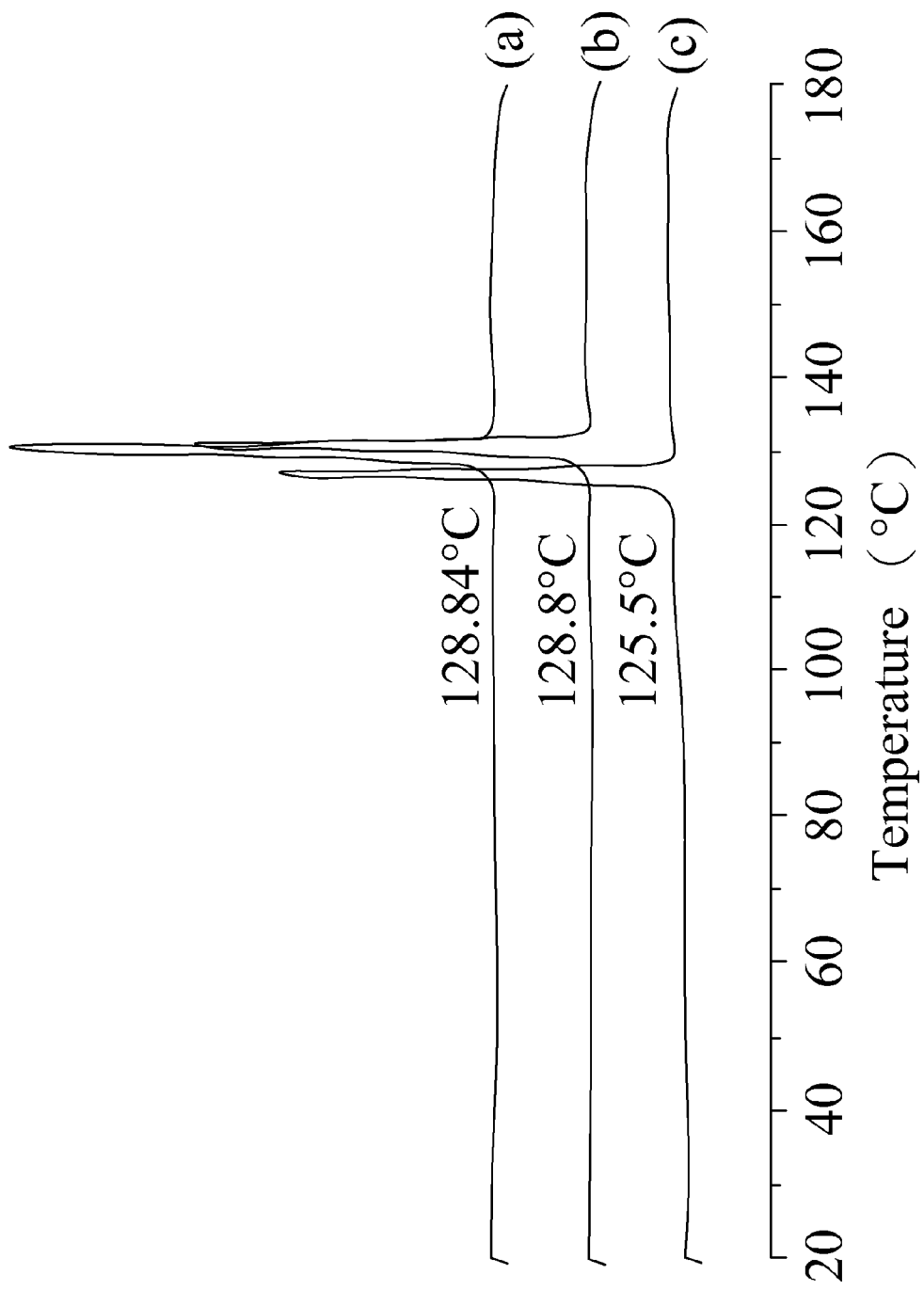
FIG. 5 is a schematic view showing the melting points of co-crystal compounds of the present invention formed by different good and bad solvents.

The inventor of the present invention further measures the melting point of the co-crystal compound of the present invention by a low-temperature differential scanning calorimeter. With reference to FIG. 5 for a schematic view showing the melting points of co-crystal compounds of the present invention formed by different good and bad solvents, the melting points of three different good and bad solvents for forming the co-crystal compound of the present invention are shown in the figure, wherein the curve (a) shows that the melting point of the co-crystal compound is equal to 128.84° C. if methanol is used as a good solvent and methyl tertiary butyl ether is used as a bad solvent; the curve (b) shows that the melting point of the co-crystal compound is equal to 128.8° C. if methanol is used as a good solvent and ethyl acetate is used as a bad solvent; and curve (c) shows that the melting point of the co-crystal compound is equal to 125.5° C. if ethanol is used as a good solvent and methyl tertiary butyl ether is used as a bad solvent. In other words, the melting point of the co-crystal compound of the present invention falls within a range of 124~130° C.

In addition, the co-crystal compound of the present invention can also be prepared by an evaporation method, and methyl tertiary butyl ether at 25° C. is used to evaporate a saturated solution of ammonium nitrate and ethanol slowly, wherein the inventor of the present invention further uses a single crystal X-ray diffraction (SXD) instrument to check the ratio of ammonium nitrate to benzo-18-crown-6-ether for preparing the co-crystal compound of the present invention by the evaporation method and finds that the ratio is equal to 1:1, and the co-crystal compound is formed with hydrogen bonding.

Figure 4:
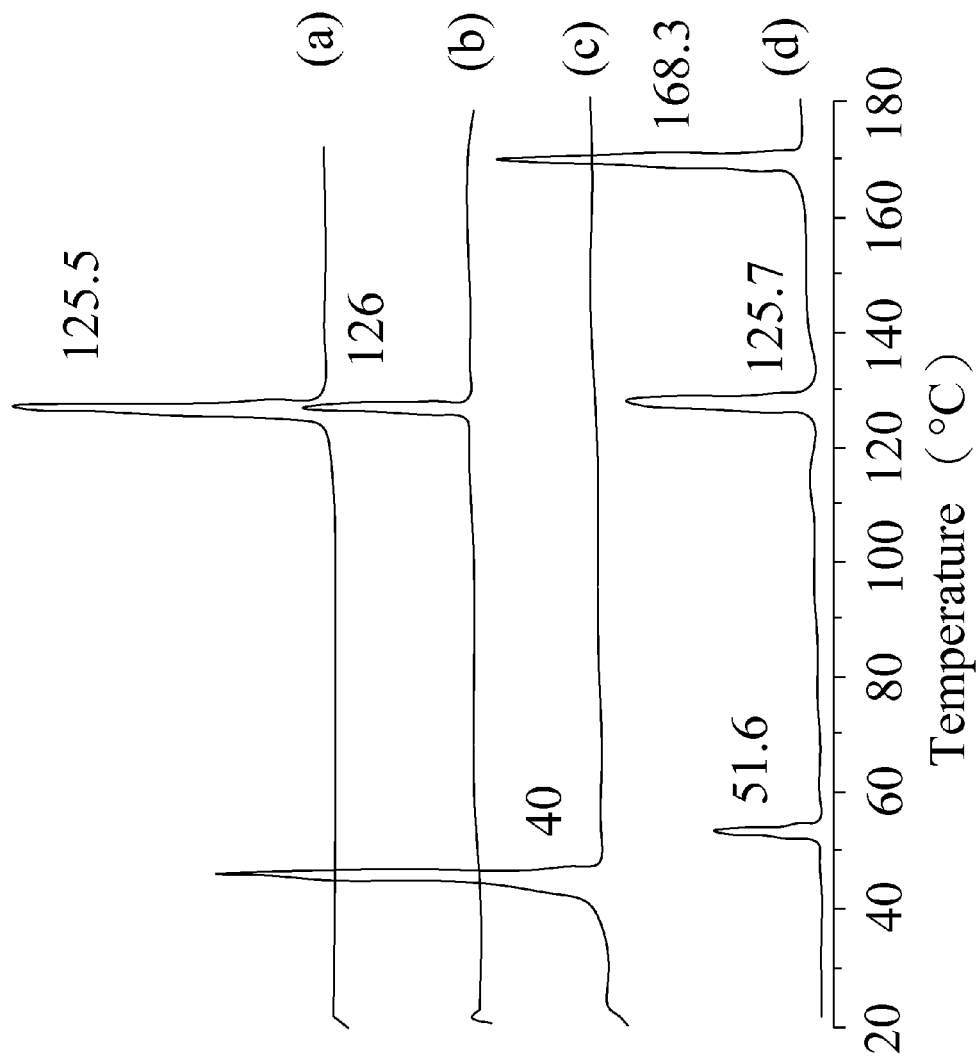
FIG. 4 is a schematic view showing a temperature versus phase transformation curve of a co-crystal compound, ammonium nitrate and benzo-18-crown-6-ether in accordance with the present invention.

In addition, the inventor of the present invention further uses the low-temperature differential scanning calorimeter to measure the melting point of the co-crystal compound of the present invention and the temperature of the phase transformation of ammonium nitrate and benzo-18-crown-6-ether. With reference to FIG. 4 for a schematic view showing a temperature versus phase transformation curve of a co-crystal compound, ammonium nitrate and benzo-18-crown-6-ether in accordance with the present invention, the curve (a) shows the melting point of the co-crystal compound of the present invention prepared by the anti-solvent method, wherein ethanol is used as a good solvent and methyl tertiary butyl ether is used as a bad solvent; the curve (b) shows the melting point of the co-crystal compound of the present invention prepared by the evaporation method; the curve (c) shows the temperature of a phase transformation of benzo-18-crown-6-ether; and the curve (d) shows the temperature of a phase transformation of ammonium nitrate.

Further, the peak value of the curve (c) does not occur on the curves (a) and (b). In the curve (d), the temperature of the phase transformation or a Form IV→Form III solid-solid phase transformation of ammonium nitrate is approximately equal to 52° C., and the temperature (approximately equal to 82° C.) of solid-solid phase transformation (Form III→Form II) and the melting point (approximately equal to 169° C.) of ammonium nitrate not longer exist in the curve (a) or the curve (b). In addition, it is noteworthy to point out that a peak value occurs at the temperature approximately equal to 125 to 126° C. in the curves (a) and (b), and this peak value has a different representative meaning from that of the curve (d). In other words, the peak value occurred at the temperature approximately equal to 125 to 126° C. in the curves (a) and (b) represents the melting point of the co-crystal compound of the present invention. On the other hand, the peak value occurred at the temperature approximately equal to 125 to 126° C. in the curve (d) represents the temperature (approximately equal to 125° C.) of the solid-solid phase transformation (Form II→Form I) of ammonium nitrate.

The present invention further provides an oxidizer of a gas generator propellant containing the aforementioned co-crystal compound.

Figure 6:
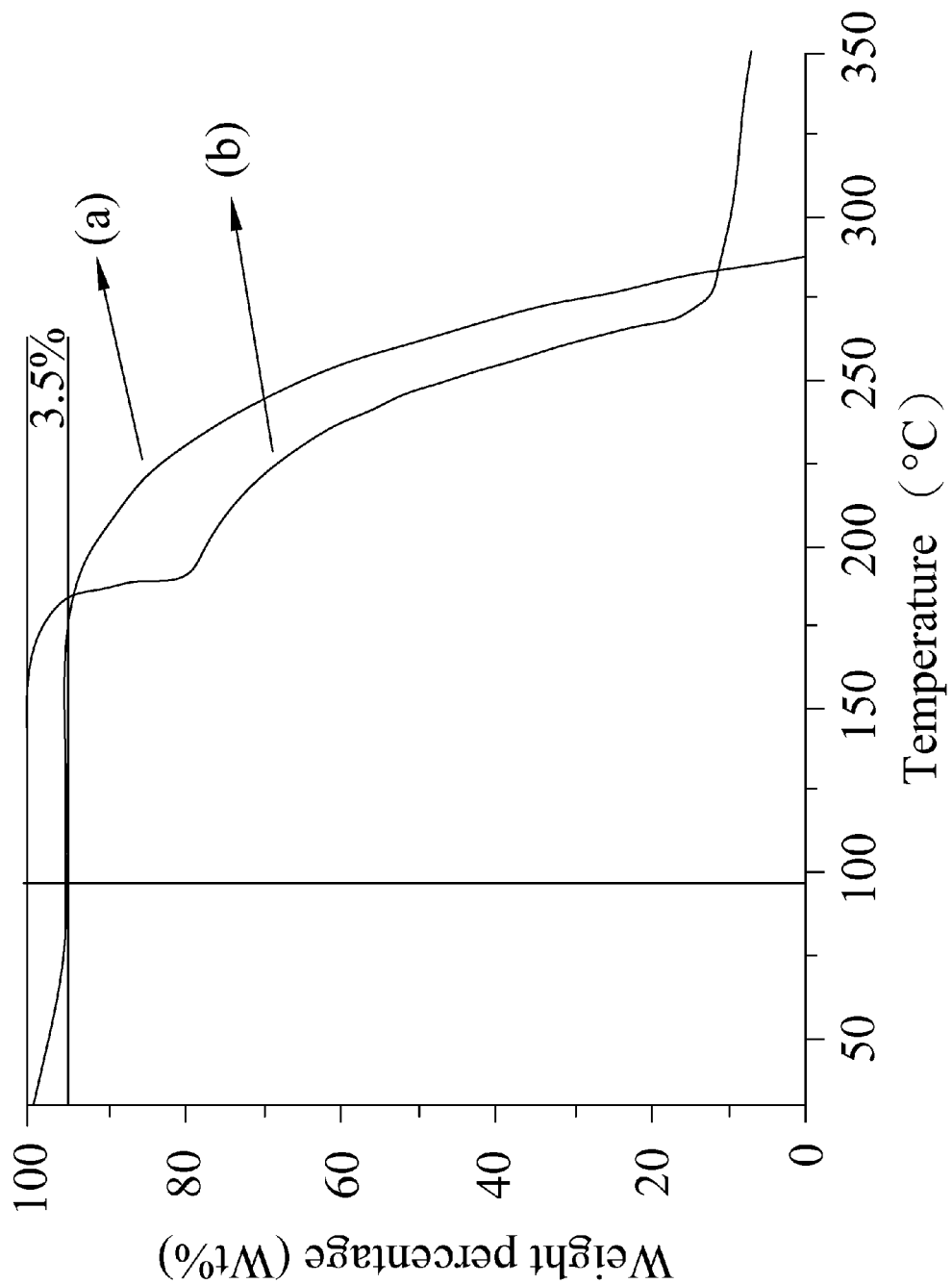
FIG. 6 is a schematic view showing test results of ammonium nitrate and a co-crystal compound of the present invention tested by a thermo gravimetric analyzer (TGA)

Firstly, the inventor of the present invention performs a hygroscopic test of the co-crystal compound of the present invention by letting ammonium nitrate and the co-crystal compound of the present invention sit still at room temperature and relative humidity of approximately 75% for approximately 12 hours, and then using a thermo gravimetric analyzer (TGA) for the test. With reference FIG. 6 for a schematic view showing test results of ammonium nitrate and a co-crystal compound of the present invention tested by a thermo gravimetric analyzer (TGA), the curve (a) represents a TGA loss curve of ammonium nitrate; the curve (b) represents a TGA loss curve of the co-crystal compound of the present invention. FIG. 6 shows that the co-crystal compound of the present invention has no weight loss before the temperature reaches 100° C., and ammonium nitrate has a weight loss of approximately 3.5%. In other words, the co-crystal compound of the present invention is non-hygroscopic.

Figure 7:
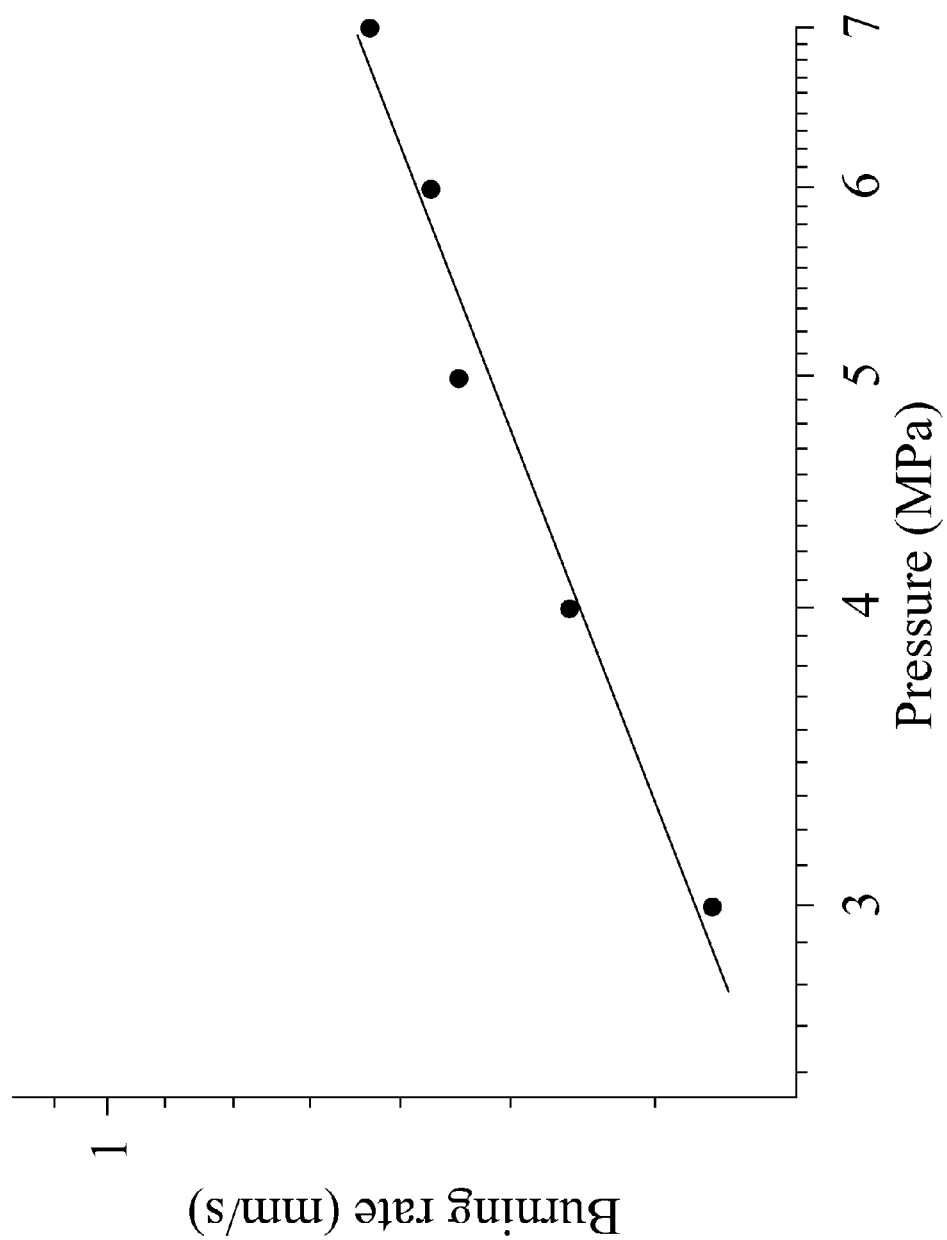
FIG. 7 is a schematic view showing test results of ammonium nitrate mixed with a co-crystal compound of 80 wt % of ammonium nitrate and 20 wt % of a co-crystal compound of the present invention test for a burning rate test.

Further, the inventor of the present invention further performs a burning rate test for the co-crystal compound. 80 wt % of ammonium nitrate and 20 wt % of the co-crystal compound of the present invention are mixed and used for the burning rate test. With reference to FIG. 7 for a schematic view showing test results of ammonium nitrate mixed with a co-crystal compound of 80 wt % of ammonium nitrate and 20 wt % of a co-crystal compound of the present invention, the mixture of 80 wt % of ammonium nitrate and 20 wt % of the co-crystal compound of the present invention has a low burning rate (7 MPa, 0.58 mm/s) and a high pressure index (n>0.6).

The data obtained above is substituted in an equation for calculating the burning rate of a general propeller, wherein the equation is r=aPn. Therefore, if the value n is large, a slight increase of the value r will increase the value P significantly, and the value P represents the pressure in a combustion chamber.

Figure 8:
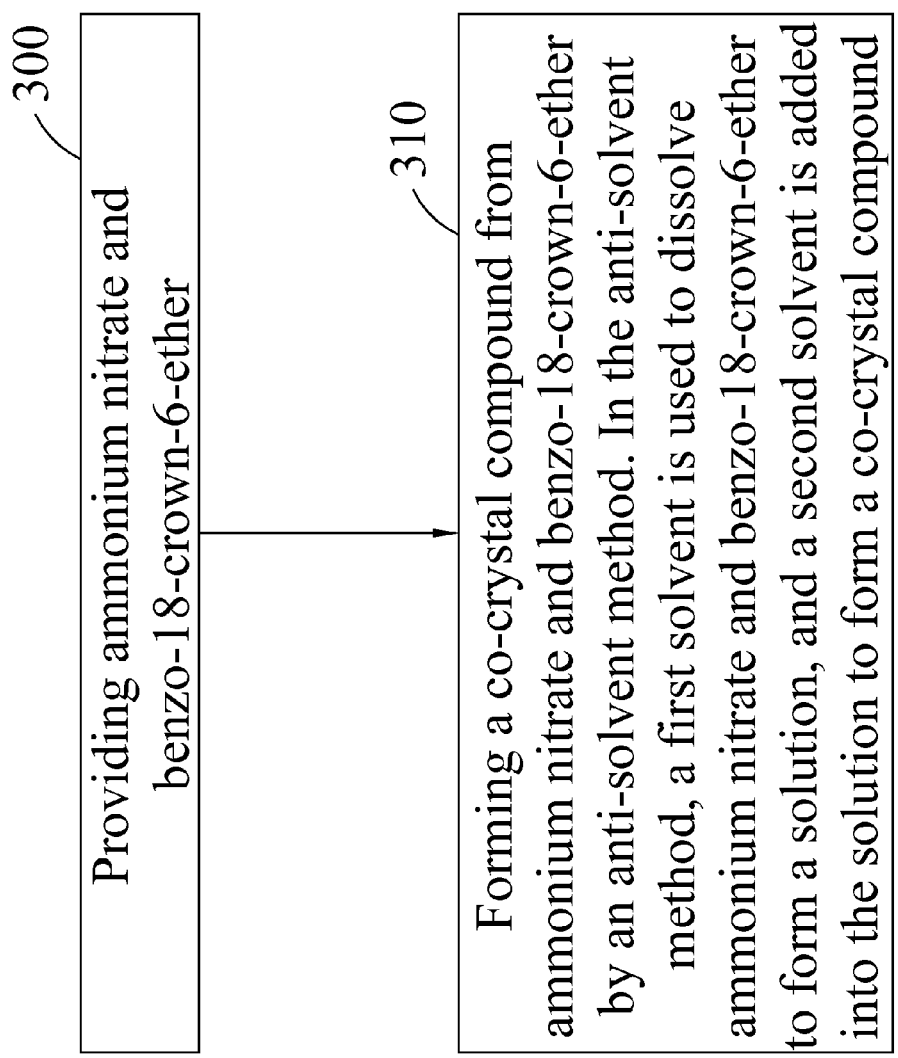
FIG. 8 is a flow chart of a method for preparing a co-crystal compound in accordance with the present invention.

With reference to FIG. 8 for a flow chart of a method for preparing a co-crystal compound in accordance with the present invention, the method for preparing a co-crystal compound comprises the following steps:

Step 300: Providing ammonium nitrate and benzo-18-crown-6-ether.

Step 310: Forming a co-crystal compound from ammonium nitrate and benzo-18-crown-6-ether by an anti-solvent method. In the anti-solvent method, a first solvent is used to dissolve ammonium nitrate and benzo-18-crown-6-ether to form a solution, and a second solvent is added into the solution to form a co-crystal compound.

In summation, the co-crystal compound of the present invention comes with a non-non-hygroscopic property, a low burning rate and a high pressure index which can be used for replacing the oxidizer of a common gas generator propellant.

What is claimed is:

1. A co-crystal compound, comprising ammonium nitrate and benzo-18-crown-6-ether, wherein characterized in that ammonium nitrate and benzo-18-crown-6-ether in a specific ratio are used to form the co-crystal compound with hydrogen bonding.

2. The co-crystal compound of claim 1, wherein the specific ratio is a mole ratio of 1:1.

3. The co-crystal compound of claim 1, wherein the co-crystal compound has a melting point falling within a range of 124~130° C.

4. The co-crystal compound of claim 1, wherein ammonium nitrate and benzo-18-crown-6-ether form the co-crystal compound by an anti-solvent method.

5. The co-crystal compound of claim 4, wherein the anti-solvent method uses a first solvent to dissolve ammonium nitrate and benzo-18-crown-6-ether to form a solution, and adds a second solvent into the solution to form the co-crystal compound.

6. The co-crystal compound of claim 5, wherein the first solvent is methanol or ethanol.

7. The co-crystal compound of claim 5, wherein the second solvent is methyl tertiary butyl ether or ethyl acetate.

8. The co-crystal compound of claim 1, wherein ammonium nitrate and benzo-18-crown-6-ether form the co-crystal compound by an evaporation method.

9. An oxidizer of a gas generator propellant, comprising a co-crystal compound according to claim 1.

10. A method for preparing a co-crystal compound, comprising the steps of:
    providing ammonium nitrate and benzo-18-crown-6-ether; and
    using ammonium nitrate and benzo-18-crown-6-ether to form a co-crystal compound by an anti-solvent method;
    wherein, the anti-solvent method uses a first solvent to dissolve ammonium nitrate and benzo-18-crown-6-ether to form a solution, and adds a second solvent into the solution to form the co-crystal compound.

* * * * *